(12) United States Patent
Doisy, III

(10) Patent No.: US 6,312,128 B1
(45) Date of Patent: Nov. 6, 2001

(54) FOCUS LIGHT FOR OPHTHALMOLOGIC MICROSCOPE

(76) Inventor: Edward A. Doisy, III, 8125 University, Clayton, MO (US) 63105

( * ) Notice: Subject to any disclaimer, the term of this patent is extended or adjusted under 35 U.S.C. 154(b) by 0 days.

(21) Appl. No.: 09/654,210

(22) Filed: Sep. 1, 2000

(51) Int. Cl.$^7$ ........................................ A61B 3/10
(52) U.S. Cl. ................................................ 351/221
(58) Field of Search .................... 351/205, 206, 351/214, 216, 221, 211; 359/381, 385, 389, 390

(56) References Cited

U.S. PATENT DOCUMENTS 5,155,509 * 10/1992 Kleinberg .............................. 351/205

* cited by examiner

Primary Examiner—George Manuel
(74) Attorney, Agent, or Firm—Blumenfeld, Kaplan & Sandweiss, P.C.

(57) ABSTRACT

A focus light is shown for use with an ophthalmologic microscope. A patient is directed to gaze at this focus light during surgery keeping his or her line of sight offset by about 18° from the illuminating light source, thus having the effect of directing a significant portion of the light source to the optic nerve instead of the macula to reduce photophobia and phototoxicity. A secondary focus light is also shown for temporarily redirecting the patient's gaze for certain incisions.

9 Claims, 2 Drawing Sheets

FOCUS LIGHT FOR OPHTHALMOLOGIC MICROSCOPE

FIELD OF THE INVENTION

The present invention relates generally to microscopes for ophthalmologic surgery and more specifically to a focus light for the same.

BACKGROUND OF THE INVENTION

Many ophthalmologic surgical procedures require the use of a microscope for the performance thereof. A conventional ophthalmologic microscope has one or more objective lenses (depending on whether it is a binocular microscope) and an illumination source. It is also well known in the art to include a gaze-fixing device with the microscope to keep the patients focus in one particular position while the surgery is performed. Often the gaze-fixing device uses the same light as the illumination source. Sometimes, the gaze-fixing light is directed through the object lens of the microscope.

It is also known to include a gaze-fixing device consisting of a light emitting diode (LED) located between the objective lens and the patient's eye, but within the light ray path of the object lens, such as that taught by Takagi et al. in U.S. Pat. No. 4,793,700. Takagi teaches a red LED focus light as a gaze-fixing device located in an optical axis of the microscope, which is particularly important in radial keratotomy (RK) surgery. The illumination source in Takagi is of the conventional type, whereby the light passes through the one of the object lenses, albeit a few degrees off of the optical axis.

Another problem with ophthalmologic microscopes is that the intense illumination source over the course of a surgical procedure, such as a cataract removal, can cause photophobia and/or phototoxicity, possibly causing a burn on the retina. This is especially true when the eye of the patient is focused in the same general direction as the illumination source, as is the case with conventional microscopes. The light from the illumination source hits the retina on the macula, which is particularly light sensitive and probably the most important part of the retina for vision.

It is known to reroute a significant portion of the illumination source so that it hits the patient's eye at an angle. This causes much of the high intensity light to hit the retina in less photosensitive areas than the macula. Such a solution is disclosed in U.S. Pat. No. 5,155,509 to Kleinberg. Such solutions are not ideal, however, because it is preferable for many types of surgery to retain a majority of the illumination source close to the visual axis of the microscope, as is the case with conventional microscopes. These solutions also lack a gaze-fixing device to keep the patient's eye from moving. Furthermore, these solutions require a complex array of mirrors and want for simplification.

Takagi purports to reduce excessive stimulus of light on the macula with the gaze-fixing device. Although such exposure may be reduced somewhat, the illumination source is still directed through the object lens, and thus not sufficiently off-angle from the optic axis to hit the insensitive optic nerve.

Thus, it is an object of the present invention to provide a gaze-fixing device for an ophthalmologic microscope that keeps the patient's focus approximately 18°–20° offset from the illumination source.

It is a further object of the present invention to provide such a gaze-fixing device that can be attached to a conventional ophthalmologic microscope.

It is yet a further object of the present invention to provide a secondary gaze-fixing device to aid the ophthalmologist in making incisions on other parts of the eye.

SUMMARY OF THE INVENTION

In keeping with the above-identified objects, the present invention is a focus light for an ophthalmologic microscope. The focus light acts as a gaze-fixing device, which attaches to most conventional ophthalmologic microscopes.

According to one aspect of the invention, the focus light is mounted on an assembly, which fastens to the objective lens of the microscope. The illuminating light source is still passed through the objective lens, but the patient is directed to focus on the focus light. The focus light is a low luminescence light offset from the optical axis of the microscope by approximately 18° and is preferably red in color. The result is that a significant portion of the illuminating light source avoids the macula and preferably hits the optic nerve where it does not damage photoreceptors, and may cause less photophobia for the patient.

According to another aspect of the invention, secondary focus lights of an alternate color are added to the assembly. When an incision needs to be made in the lower (or even upper) portion of the eye, the patient is directed to temporarily focus on the secondary focus light.

According to yet another aspect of the present invention, two secondary focus lights are used. One is located on either side of the primary focus light on the assembly. Thus, the same assembly can be used by either a left-handed or right-handed ophthalmologist.

BRIEF DESCRIPTION OF THE DRAWINGS

The above-mentioned and other features, advantages and objects of this invention, and in the manner in which they are obtained, will become more apparent and will be best understood by reference to the detailed description in conjunction with the accompanying drawings which follow, wherein.

DETAILED DESCRIPTION OF THE DRAWINGS

Figure 1:
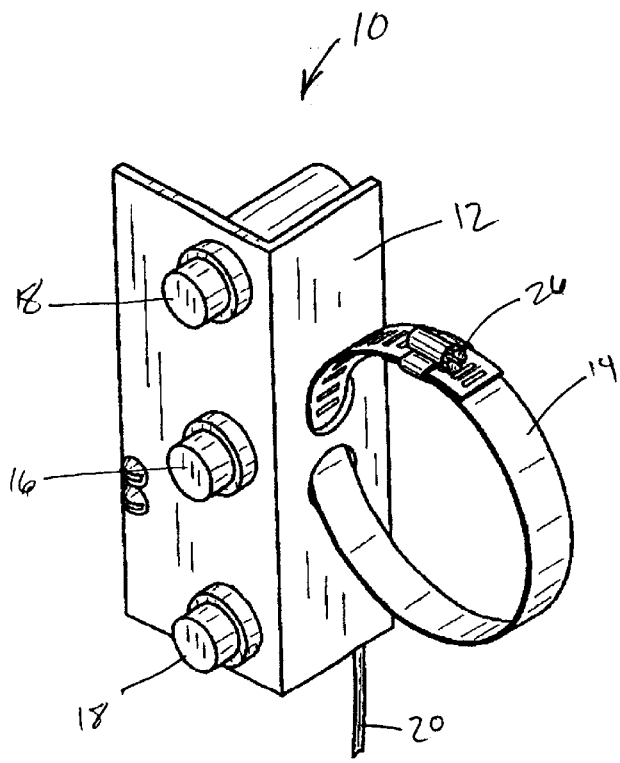
FIG. 1 is an isometric view of the focus light assembly incorporating the present invention.
Figure 2:
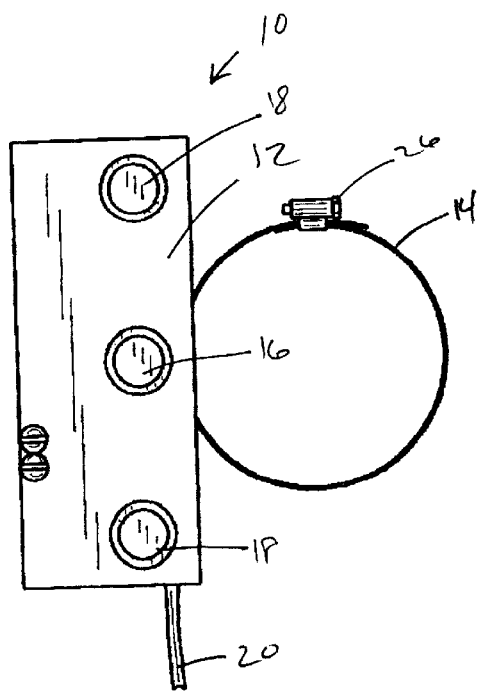
FIG. 2 is a front view of the focus light assembly of FIG. 1.
Figure 3:
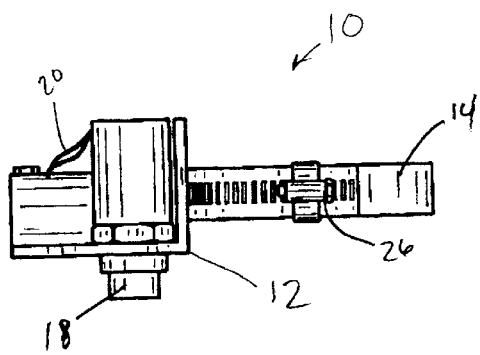
FIG. 3 is a side view of the focus light assembly of FIG. 1.
Figure 4:
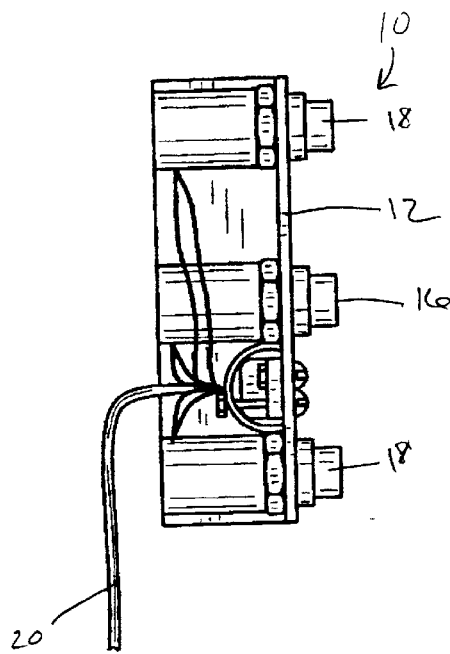
FIG. 4 is a top view of the focus light assembly of FIG. 1.

Referring now to FIGS. 1–4, a focus light assembly 10 is shown generally. The assembly 10 comprises a base 12 and a fastener 14. Located on the base 12 is a primary focus light 16, and optionally one or more secondary focus lights 18. The primary focus light 16 is a low luminescence light source such as an LED or a low power light bulb (that for safety purposes should use no more than approximately 18 volts). In the preferred embodiment the primary focus light 16 is red in color, as the wavelength of red light causes among the least amount of phototoxicity. Additionally, the red wavelength (between 650 nm and 700 nm) can usually be distinguished through a patient's cataract better than other colors.

The secondary focus lights 18 may be any color, the inventor has found green to work especially well. In the preferred embodiment there are two secondary focus lights 18 for reasons stated later. The focus lights 16 and 18 also have power leads 20 protruding therefrom, which are connected to a suitable power source, the selection of which is a simple matter of choice to anyone of ordinary skill in the art.

Figure 5:
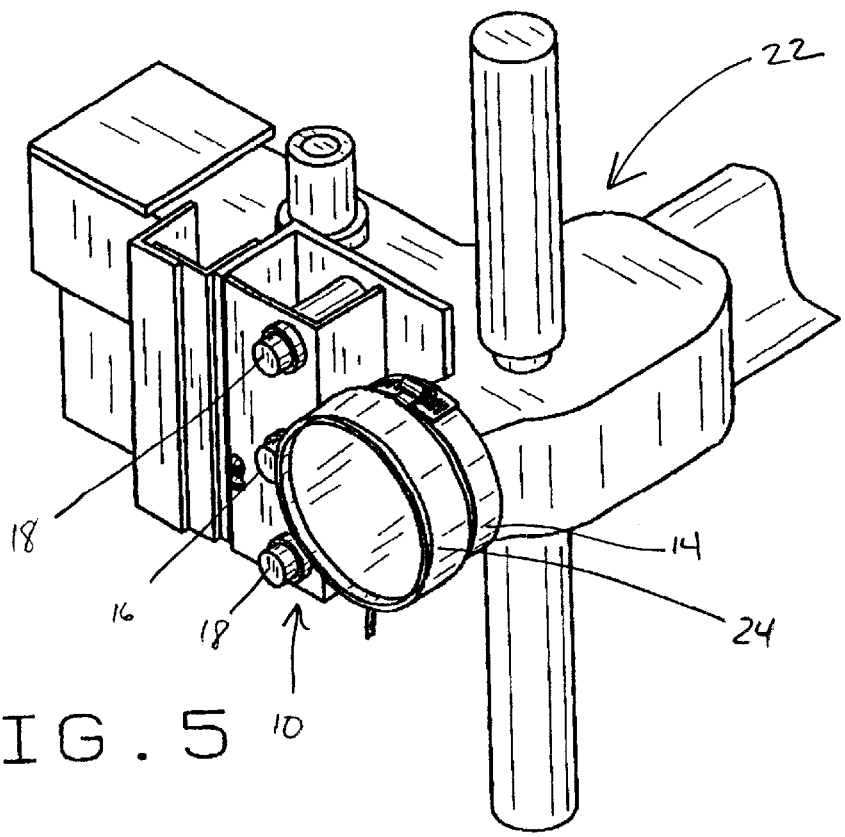
FIG. 5 is an isometric view of the focus light assembly of FIG. 1 as installed on a conventional ophthalmologic microscope.

The focus light assembly 10 is fastened to most any conventional ophthalmologic microscope 22, as seen in FIG. 5. The conventional microscope 22 has an objective lens 24 and an illuminating light source (not shown) for the surgeon that is transmitted through the objective lens 24. The fastener 14 is typically clamped around the objective lens 24 of the microscope 22. Shown in the preferred embodiment is a standard cylindrical clamp, which is tightened by rotating clamping screw 26 with a screwdriver or wrench.

Figure 6:
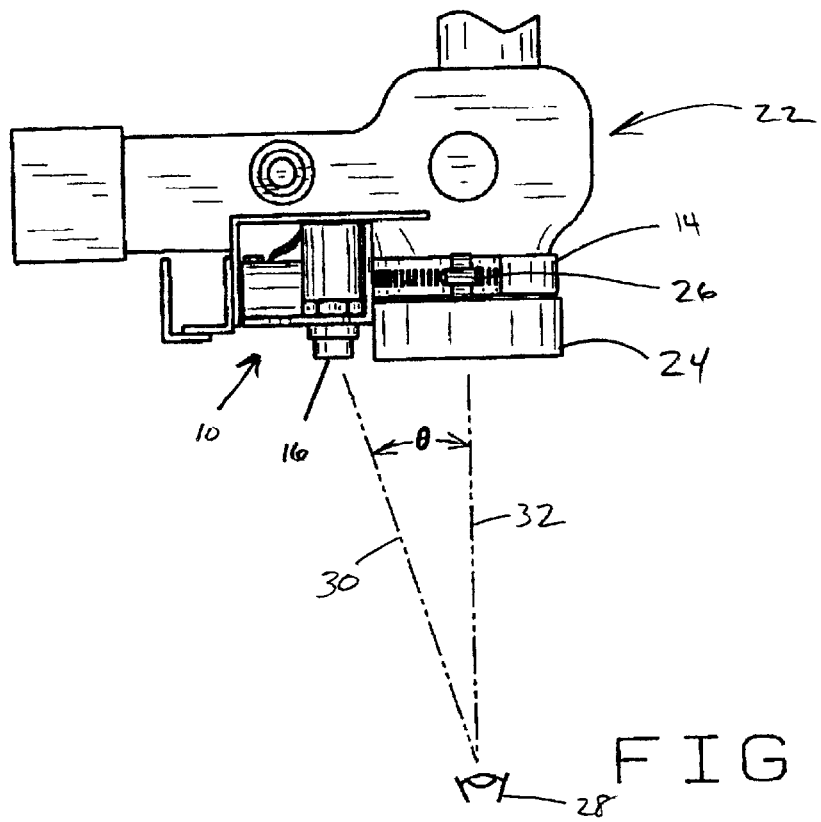
FIG. 6 is a side view of the focus light assembly and microscope of FIG. 5, indicating the relationship with a patient's eye.

During the majority of the duration of the surgery, the patient is instructed to focus on the primary focus light 16. FIG. 6 shows the relationship between the patient's eye 28, the primary focus light 16, and the objective lens 24. The patient's line of sight is shown by line 30 and the optical axis of the microscope (and consequently the illuminating light source) is shown by line 32. The resulting angle, designated by theta, is between 17° and 20°, and most preferably, approximately 18°.

This angle results in the patient's eye 28 being exposed to the primary focus light 16 on the fovea macula of the retina. Meanwhile, the bright illuminating light source hits the retina 18° offset from the macula, on the optic nerve. Thus, the illuminating light source causes less phototoxicity or photophobia.

One or more secondary focus lights 18 are optionally placed a few inches apart from the primary focus light 16, preferably around two inches. During surgeries such as cataract removal the ophthalmologist may need to make one or more incisions on the lower part of the eye 28. The patient is asked to temporarily refocus their attention up on the secondary focus light 18, which is preferably a different color, such as green so that the patient may be easily instructed to switch between the primary and secondary focus lights 16 and 18.

The use of two secondary focus lights 18 serves multiple purposes. Two secondary focus lights 18 located on either side of the primary focus light, allow the same assembly 10 to be used for left-handed and right-handed ophthalmologists. The additional secondary focus light 18 also allows the ophthalmologists who wish to make incisions in the upper part of the eye 28 to direct the patient to temporarily switch focus downward (instead of upward) to the alternate secondary focus light 18.

It should be appreciated that the exact size of the base 12 and the location of the primary focus light 16 on the assembly 10 may vary depending upon the microscope 22 being used. In particular, the thickness of the housing of the objective lens 24 and the focal length of the microscope 22 will affect the size and configuration parameters of the assembly 10. The important principal is that the patient's line of sight 30 to the primary focus light 16 should be in the vicinity of 18° offset from the illuminating light axis 32 of the microscope 22 when the patient is in the operating position.

It should also be noted that with the present invention in its preferred advantage in that red is a relatively easy color for cataract patients to see. It should also be noted that the surgeon has a brighter red reflex when the illuminating light is reflected from the optic nerve. This makes for better visualization of the capsule of the cataract, particularly in patients with significant skin pigmentation.

Accordingly, while this invention is described with reference to a preferred embodiment of the invention, it is not intended to be construed in a limiting sense. It is rather intended to cover any variations, uses or adaptations in the invention utilizing its general principles. Various modifications will be apparent to persons skilled in the art upon reference to this description. It is therefore contemplated that the appended, and any claims will cover any such modifications or embodiments as fall within the true scope of the invention.

I claim:

1. A focus light assembly for an ophthalmologic microscope comprising:

a base;

at least one focus light affixed to said base, said focus light adapted to keep at least one eye of a patient focused thereon; and a fastener extending from said base and adapted to fasten the assembly to the ophthalmologic microscope such that said focus light becomes offset from an optical axis of the microscope by an angle between 17° and 20°.

2. The focus light assembly of claim 1, wherein the microscope has direct illumination means coaxial with an optical axis thereof.

3. The focus light assembly of claim 2, wherein said assembly is adapted to be retrofitted on an existing microscope.

4. The focus light assembly of claim 2, wherein said focus light is red in color.

5. The focus light assembly of claim 2, further comprising exactly three focus lights, wherein one of said focus lights is designated a primary focus light and the remainder of said focus lights are designated secondary focus lights.

6. The focus light assembly of claim 5, wherein said focus lights are configured linearly with said primary focus light in the middle.

7. The focus light assembly of claim 6, wherein said primary focus light is red in color.

8. The focus light assembly of claim 7, wherein said secondary lights are a color other than red.

9. The focus light assembly of claim 8, wherein said secondary light are green in color.

* * * * *